US009933377B2

(12) United States Patent
Luxbacher

(10) Patent No.: US 9,933,377 B2
(45) Date of Patent: Apr. 3, 2018

(54) SYSTEM FOR DETERMINING THE ZETA POTENTIAL FOR CHARACTERIZING A SOLID/LIQUID INTERFACE WITH CONTROLLED PROFILE PRESSURE LOADING

(71) Applicant: Anton Paar GmbH, Graz (AT)

(72) Inventor: Thomas Luxbacher, Graz (AT)

(73) Assignee: Anton Paar GmbH, Graz (AT)

( * ) Notice: Subject to any disclaimer, the term of this patent is extended or adjusted under 35 U.S.C. 154(b) by 239 days.

(21) Appl. No.: 14/711,006

(22) Filed: May 13, 2015

(65) Prior Publication Data

US 2015/0330925 A1  Nov. 19, 2015

(30) Foreign Application Priority Data

May 13, 2014  (AT) .................................. 50336/2014

(51) Int. Cl.
 *G01N 27/00* (2006.01)
 *G01N 27/60* (2006.01)
 G01N 27/447 (2006.01)

(52) U.S. Cl.
 CPC ............. *G01N 27/00* (2013.01); *G01N 27/60* (2013.01); *G01N 27/44752* (2013.01)

(58) Field of Classification Search
 CPC . D21H 23/08; G01N 27/447; G01N 27/44752
 See application file for complete search history.

(56) References Cited

U.S. PATENT DOCUMENTS 5,171,134 A * 12/1992 Morgart .............. F04B 11/0016
 417/540
6,023,661 A    2/2000 Sottery

FOREIGN PATENT DOCUMENTS

DE   DD 258 470 A1   7/1988
DE   10154790 A1   11/2001
DE   202 09 563 U1   2/2003
(Continued)

OTHER PUBLICATIONS

Hasselbrink et al., "Microscale Zeta Potential Evaluations Using Streaming Current Measurements," Sandia Report SAND2001-8193, printed May 2001.*

(Continued)

*Primary Examiner* — Alexander S Noguerola
(74) *Attorney, Agent, or Firm* — Robert A. Blaha; Smith Tempel Blaha LLC

(57) ABSTRACT

A device determines information indicative for a zeta potential at the interface between a solid phase and a liquid phase. The device includes a pressure vessel, in which the liquid phase can be accommodated and a measuring cell, downstream of the pressure vessel and such that it can be brought into fluid communication with the pressure vessel and in which the solid phase can be accommodated. A storage vessel is downstream of and in fluid communication with the measuring cell. A pressure loading apparatus, loads the pressure vessel with a pressure profile with a temporally continuous pressure change so a liquid phase can be conveyed out of the pressure vessel through the measuring cell into the storage vessel. A detection apparatus detects the information indicative for the zeta potential at the measuring cell during the loading of the pressure vessel with the pressure profile.

20 Claims, 7 Drawing Sheets

(56) References Cited

FOREIGN PATENT DOCUMENTS

| JP | S62-47545 A | 3/1987 |
|---|---|---|
| JP | 2216442 A | 8/1990 |
| JP | 2216443 A | 8/1990 |
| JP | 0450758 A | 2/1992 |
| JP | 11190711 A | 12/1997 |
| WO | WO8600707 A1 | 1/1986 |
| WO | WO2007065825 A1 | 6/2007 |

OTHER PUBLICATIONS

Lin et al., "Tuning the surface potential of gold substrates arbitrarily with self-assembled monolayers with mixed functional groups," Phys. Chem. Chem. Phys. 2009, 11, 6199-6204.*

Kirby et al., "Review—Zeta potential of microfluidic substrates: 1. Theory, experimental techniques, and effects on separations", Electrophoresis 2004, 25, 187-202.*

Temmel et al., "Zeta Potential of Photochemically Modified Polymer Surfaces," Progr. Colloid Polym. Sci. (2006) 132: 54-61.*

Manns et al., "Information on Conductivity Measurement," Jumo, FAS 624, Edition Apr. 2007, Apr. 2007.*

Zimmerman, Ralph et al., Determination of the Zeta Potential and the Surface Conductivity by Streaming Potential and Streaming Current Measurements, Technisches Messen, 2000, pp. 353-360, vol. 9, Oldenbourg Verlag.

Pu, Q. et al., Label-Free Detection of Heparin, Streptavdin, and Other Probes by Pulsed Streaming Potentials in Plastic Microfluidic Channels, Analytical Chemistry, 6532-6536, vol. 80, No. 17, Sep. 1, 2008, American Chemical Society, published on Web Jul. 31, 2008.

Luna-Vera, F. et al., Adsorption Kinetics of Proteins in Plastic Microfluidic Channels: Real-time Monitoring of Lysozyme Adsorption by Pulsed Streaming Potentials, Biosensors and Bioelectronics, 1539-1543, 25 (2010), Elsevier B.V., available online Nov. 10, 2009.

Gupta, M.L. et al., Quantifying Surface-Accessible Quaternary Charge for Surface Modified Coatings via Streaming Potential Measurements, LAngmuir 2010, vol. 26, No. 11, 9032-9039, American Chemical Society, published on Web Mar. 24, 2010.

Werner et al., Extended Electrokinetic Characterization of Flat Solid Surfaces, Journal of Colloid and Interfaces Science 208, 329-346 (1998).

* cited by examiner

SYSTEM FOR DETERMINING THE ZETA POTENTIAL FOR CHARACTERIZING A SOLID/LIQUID INTERFACE WITH CONTROLLED PROFILE PRESSURE LOADING

CROSS-REFERENCE TO RELATED APPLICATION

This application claims the benefit of the filing date of Austrian Patent Application No. 50336/2014 filed 13 May 2014, the disclosure of which is hereby incorporated herein by reference.

TECHNICAL FIELD

Embodiments of the invention relate to a device and a method for determining information being indicative for a zeta potential, for characterising the interface between a solid phase and a liquid phase.

TECHNOLOGICAL BACKGROUND

The electrokinetic or zeta potential describes the charge distribution at the interface of two immiscible phases. The zeta potential is important for the characterisation of the solid/liquid interface. The zeta potential can be calculated at the interface between a macroscopic material surface and a liquid from measurements of the streaming potential and the streaming current. Materials with macroscopic surfaces are to be assigned to test samples of different shape and size. These include samples with a flat surface, fibre samples, granulate and powders with a particle size larger than 1 μm (=1·10$^{-6}$ m).

For measuring the streaming potential and streaming current, the solid sample can be arranged in a measuring cell in such a manner that a capillary or a capillary system with suitable hydraulic permeability is created. The liquid flow through this capillary (flow channel) creates a pressure difference and an electrical signal, which is measured either as voltage (streaming potential) or current (streaming current). Solids with a flat surface are for example arranged parallel next to one another and a capillary with rectangular cross-sectional area results. Fibre samples and granulate are arranged in the form of a plug for example and the liquid flows through the irregular capillary system created thereby.

The zeta potential is calculated according to the classical equations of Helmholtz and Smoluchowski. The following applies for calculation from measurements of the streaming current $I_{str}$:

$$\zeta = \frac{dI_{str}}{d\Delta p} \cdot \frac{\eta}{\varepsilon \cdot \varepsilon_0} \cdot \frac{L}{A} \quad \text{(Equation 1)}$$

wherein $dI_{str}/d\Delta p$ is the streaming current coefficient (change of the streaming current with pressure difference over the length of the flow channel), $\eta$ is the dynamic viscosity of the liquid, $\varepsilon$ is the dielectric coefficient of the liquid, $\varepsilon_0$ is the permittivity, L is the length of the flow channel, A is the cross section of the flow channel.

The calculation of the zeta potential takes place from measurements of the streaming potential $U_{str}$ according to:

$$\zeta = \frac{dU_{str}}{d\Delta p} \cdot \frac{\eta}{\varepsilon \cdot \varepsilon_0} \cdot \kappa \quad \text{(Equation 2)}$$

wherein $dU_{str}/d\Delta p$ is the streaming potential coefficient (change of the streaming potential with pressure difference over the length of the flow channel), $\kappa$ is the electrical conductivity of the liquid.

The relationship between the zeta potential and the streaming current (Equation 1) or streaming potential (Equation 2) only leads to identical results if the solid sample is non-conductive. The identity of the zeta potential values is additionally dependent on the electrolyte concentration. The surface or interfacial conductivity influences the correct determination of the zeta potential according to Equation 2 in particular in the case of low ionic strength (I<0.001 mol/l). The zeta potential of conductive solid surfaces (electronically conductive, for example metals, or ionically conductive, for example porous solids or swellable layers or materials) cannot be determined correctly even at higher ionic strengths (I≥0.001 mol/l) according to Equation 2. These limitations necessitate the measurement of the streaming current instead of the streaming potential and the calculation of the zeta potential according to Equation 1.

The measurement of streaming potential and streaming current takes place for example using measuring electrodes made from different materials and with a different size and construction. Electrodes are subject to the process of polarisation, which can have various causes:

Either electrodes of a first type (for example platinum electrodes) or electrodes of a second type (reversible electrodes, for example silver/silver chloride electrodes) are used. Polarisation effects occur in the case of electrodes of the first type in particular and less markedly in the case of electrodes of the second type.

The electrode polarisation is also dependent on the specific surface of the electrodes. Thus, for example, the surface of platinum electrodes (electrodes of the first type) is enlarged by electrochemical application of a porous platinum layer (platinum black). The surface of the silver chloride layer deposited for example on silver electrodes is likewise porous and thereby reduces the tendency to electrode polarisation.

Electrode polarisation is principally a characteristic of electrolyte concentration (ionic strength). Polarisation effects occur on electrodes of the first type even at low ionic strength of an electrolyte dissolved in water. Depending on the quality (size, quality of the coating) and specific surface, the electrode polarisation also increases considerably for electrodes of the second type above a certain ionic strength.

The tendency to polarisation effects of electrodes has an influence both on the measurement of the streaming current and on the measurement of the streaming potential. The influence on the current measurement is occasionally larger than that on the voltage measurement. For small measurement signals of the streaming potential and streaming current, the electrode polarisation increases the error in the measurement and consequently reduces the quality of the zeta potential calculated according to Equation 1 or Equation 2.

There is a series of commercial measuring devices for measuring the streaming potential, but also the streaming current for determining the zeta potential at macroscopic solid surfaces. In these measuring devices, the effect of the electrode polarisation, described by the difference in the electric potential between the two measuring electrodes in the rest state, is counteracted by corresponding structural measures and measurement protocols.

In the case of a two-point measurement, the voltage value in the rest state (no fluid flow, asymmetry potential $U_0$) and the streaming potential at a constant pressure difference, $U_{str}(\Delta p)$ are used in order to calculate the streaming potential coefficients in Equation 2 as a differential quotient $\Delta U_{str}/\Delta p$, where $\Delta U_{str}=U_{str}(\Delta p)-U_0$. This method is suitable for measurement conditions, in which the asymmetry potential $U_0$ results into a small contribution to the measured streaming potential (<10%).

In the case of a pressure stage measurement, the streaming potential $U_{str}(\Delta p)$ is determined at different constant pressure differences and the streaming potential coefficient is calculated in Equation 2 from the linear regression of the measured points $U_{str}$ versus $\Delta p$. Due to the larger number of measurement points compared to the two-point measurement, the quality of the calculated streaming potential coefficient is improved.

The technical realisation of such methods for determining the streaming potential and streaming current coefficients takes place in commercial measuring devices and provisional measurement apparatus by applying a pressure difference by means of an external pump or gas pressure.

The measurement of the streaming potential and the streaming current according to conventional measuring methods is limited to the determination of the zeta potential at low ionic strengths however.

Further prior art is disclosed in WO 86/00707, Pu et al., "Label-free detection of heparin, streptavidin, and other probes by pulsed streaming potenzials in plastic microfluidic channels", Anal Chem 2008 Sep. 1; 80(17):65326, Luna-Vera et al., "Adsorption kinetics of proteins in plastic microfluidic channels: Real-time monitoring of lysozyme adsorption by pulsed streaming potenzials", Biosensors and Bioelectronics 25 (2010) 1539-1543, JPH02216443 and U.S. Pat. No. 6,023,661.

SUMMARY OF THE INVENTION

There may be a need to enable the determination of information being indicative for a zeta potential for characterising a solid/liquid sample with high accuracy and in particular also for high ionic strengths.

This need is solved by means of the subject matters with the features according to the independent patent claims. Further exemplary embodiments are shown in the dependent claims.

According to an exemplary embodiment of the present invention, a device is provided for determining information being indicative for a zeta potential for characterising the interface between a solid phase and a liquid phase, wherein the device comprises a pressure vessel, in which the liquid phase can be accommodated; a measuring cell, which is arranged downstream of the pressure vessel and can be brought into fluid communication with the pressure vessel or is in fluid communication with the pressure vessel and in which the solid phase can be accommodated; a storage vessel, which is arranged downstream of the measuring cell and is in fluid communication with the measuring cell or can be brought into communication with the measuring cell, a pressure loading apparatus, which is configured for loading the pressure vessel with a pressure profile with a temporally continuous pressure change in such a manner that, as a consequence, liquid phase can be conveyed out of the pressure vessel through the measuring cell into the storage vessel; and a detection apparatus for detecting the information being indicative for the zeta potential at the measuring cell during the loading of the pressure vessel with the pressure profile.

According to a further exemplary embodiment of the present invention, a method is provided for determining information being indicative for a zeta potential for characterising the interface between a solid phase and a liquid phase, wherein in the method the liquid phase is accommodated in a pressure vessel; the solid phase is accommodated in a measuring cell, which is arranged downstream of the pressure vessel and can be brought into fluid communication with the pressure vessel or is in fluid communication with the pressure vessel, a storage vessel is arranged downstream of the measuring cell and can be brought into fluid communication with the measuring cell or is in fluid communication with the measuring cell; the pressure vessel is loaded with a pressure profile with a temporally continuous pressure change in such a manner that the liquid phase can consequently be conveyed out of the pressure vessel through the measuring cell and into the storage container; and the information being indicative for the zeta potential is detected at the measuring cell during the loading of the pressure vessel with the pressure profile.

According to one exemplary embodiment, in order to characterise an interface between a solid phase and a liquid phase, information about an associated zeta potential can be determined in that a temporally continuous change of the pressure difference (in particular with the stipulation of a pressure gradient changing over the measurement) between the pressure vessel and the storage vessel is set or predetermined by means of control technology during the carrying out of the measurement. As a result, time-dependent influences of electrode polarisation and other drift phenomena can be compensated at least to some extent. This leads to a higher accuracy and reliability of the determined measurement results, even in the case of higher ionic strengths.

Additional exemplary embodiments of the invention and the method are described below.

According to an exemplary embodiment of the invention, the pressure loading apparatus can be configured to provide the measuring cell with a pressure profile with a pulse-free pressure change, in particular with a monotonous (in particular monotonously decreasing), for example linear pressure curve. If the pressure difference between the pressure vessel and storage container that changes over time changes without pressure pulses or other discontinuities in the pressure/time curve, the measurement can be carried out in a manner free of artefacts and therefore highly accurately or reproducibly.

According to an exemplary embodiment of the invention, the pressure loading apparatus can be configured to load a gas chamber above the liquid phase in the pressure vessel with a compressed gas cushion, in order to, as a consequence, generate the pressure profile with a continuous drop of the pressure. An overpressure can prevail in the interior of the pressure vessel, wherein the interior of the pressure vessel is pressure-decoupled from the environment. In other words, a gas cushion, which is at increased pressure compared to the atmosphere, is applied to the liquid column in the pressure vessel. This pressure drops continuously when the liquid phase flows out of the pressure vessel through the measuring cell into the storage vessel, which is at a reference pressure for example (for example connected to atmospheric pressure).

According to an exemplary embodiment of the invention, the pressure loading apparatus may comprise a pressure generation unit for generating pressure in the pressure vessel and a fluid switching element, so that by switching the switching element for fluid coupling of the pressure vessel with the measuring cell, the measuring cell can be loaded with the liquid phase in accordance with the pressure profile. The switching element may be a fluid switching element (in particular a fluid valve that can be controlled or switched using a control apparatus) in a fluid path, which selectively permits or prevents a fluid flow and an at least partial pressure equalisation through the fluid path, depending on the switching state.

According to an exemplary embodiment of the invention, the switching element can be arranged between the pressure vessel and the measuring cell. As a result, the pressure can be applied to the pressure vessel until the same has reached a desired initial value. By subsequent switching the switching element in order to bring the pressure vessel into fluid communication with the measuring cell, the pressure profile can then be applied in a defined manner to the measuring cell.

According to an exemplary embodiment of the invention, during the pressure change, it is possible to change in an alternating manner between an operating mode permitting a fluid connection between the pressure vessel and the measuring cell and an operating mode preventing a fluid connection between the pressure vessel and the measuring cell, in order to detect, in the operating mode preventing the fluid connection, a baseline signal and thereby to correct a measurement signal detected in the operating mode permitting the fluid connection. This can be achieved by a corresponding switching of the switching element between the pressure vessel and the measuring cell.

According to an exemplary embodiment of the invention, the pressure generation unit can be selected from a group, which consists of a pump, in particular a membrane pump, and/or a gas pressure supply, in particular a gas bottle (for example a nitrogen gas bottle). The pressure generation unit can be selectively or controllably fluid coupled with the pressure vessel or fluid decoupled therefrom.

According to an exemplary embodiment of the invention, the device can have a pressure measuring unit for detecting the pressure curve according to the loaded pressure profile, in particular upstream of or at the pressure vessel. According to an exemplary embodiment of the invention, the switching element can be switched in such a manner by means of a control apparatus, to which the detected pressure value is transmitted by the pressure measuring unit, that the switching element activates the fluid connection between the pressure vessel and the measuring cell in the event of an exceedance of a predetermined pressure value detected by means of the pressure measuring unit. The pressure value or pressure threshold value can be the desired initial value of the pressure profile, with which the fluid phase is conveyed through the measuring cell at the start of the zeta potential measurement.

According to an exemplary embodiment of the invention, the storage vessel can be configured to be free from overpressure, in particular, the interior thereof is at atmospheric pressure or at different low pressure (compared to the pressure vessel). The pressure vessel can therefore be depressurised or brought to a pressure level, which is defined by the reservoir-like pressure conditions in the environment. In this way, if the pressure value drops continuously at the input side at the measuring cell, a constant pressure can be predetermined at the output side in this manner, as a result of which, the temporally continuously dropping pressure profile is set.

According to an exemplary embodiment of the invention, the detection apparatus can be configured for detecting the information being indicative for the zeta potential on the basis of Equation 1 and Equation 2. The evaluation methodology illustrated in the introduction of this description can therefore also be applied to exemplary embodiments of the invention and should in this respect also be understood as being disclosed in connection with exemplary embodiments of the invention.

According to an exemplary embodiment of the invention, the detection apparatus can be configured for detecting the information being indicative for the zeta potential on the basis of a current measurement and on the basis of a voltage measurement at the measuring cell. The zeta potential being indicative for the interfacial properties can be determined on the basis of the value of the electric current and the electric voltage at a measuring cell made up of a liquid phase mixed with a solid phase.

According to an exemplary embodiment of the invention, the device can comprise an input electrode at an input of the measuring cell and an output electrode at an output of the measuring cell, wherein the detection apparatus for detecting the information being indicative for the zeta potential is arranged between the input electrode and the output electrode. The input electrode and/or output electrode can be designed as an electrode of the first type or an electrode of the second type. According to an exemplary embodiment of the invention, the input electrode for interacting at least with the liquid phase can be arranged at the input of the measuring cell and the output electrode for interacting at least with the liquid phase can be arranged at the output of the measuring cell.

According to an exemplary embodiment of the invention, the detection apparatus can be constructed to detect information being indicative for an electrical resistance of the solid phase and the liquid phase in the measuring cell by means of the input electrode and by means of the output electrode (in particular additionally). According to an exemplary embodiment of the invention, the detection apparatus can be configured to derive, on the basis of the information being indicative for the electrical resistance, at least one piece of information, which is selected from a group, which consists of information regarding the presence or absence of gas bubbles in the measuring cell, and a contribution of one of the phases (in particular the solid phase) to the total electrical conductivity. The electrical resistance can deliver the basis for more in-depth information in connection with the characterisation of the solid/liquid interface.

According to an exemplary embodiment of the invention, the device can comprise a liquid-phase return mechanism for returning liquid phase from the storage vessel to the pressure vessel. In this manner, the measured liquid phase can be returned and reused. As a result, multiple measurement of a liquid sample is enabled, so that smaller amounts of liquid sample are sufficient and the waste quantities arising are kept small. The liquid-phase return mechanism can in particular also synergistically use a pump for returning, which is used for pressure loading the pressure vessel, (in particular during operation with a reversed delivery direction).

According to an exemplary embodiment of the invention, the switching element can be arranged in a fluid path, in which liquid phase can be returned from the storage vessel to the pressure vessel by means of the liquid-phase return mechanism. Thus, the switching element can also be used synergistically, in order not only to predetermine the start of the measurement of the information being indicative for the zeta potential by means of a switching process, but rather also to enable a returning of measured liquid phase to the pressure vessel in a different switching state without further switching elements or additional fluid lines.

According to an exemplary embodiment of the invention, the device can furthermore have a further pressure vessel, in which a further liquid phase can be accommodated, and a further measuring cell, which is arranged downstream of the further pressure vessel and can be brought into fluid communication with the further pressure vessel and in which the further solid phase can be accommodated, wherein the pressure loading apparatus for loading the further pressure vessel with a pressure profile with a temporally continuous pressure change is configured in such a manner that the further liquid phase can thereby be conveyed out of the further pressure vessel through the further measuring cell, and wherein the detection apparatus is configured for detecting information being indicative for the zeta potential at the further measuring cell during the loading of the further pressure vessel with the pressure profile. In this manner, one and the same pressure generating apparatus and if appropriate one and the same storage container can be used for a plurality of measurement paths, as a result of which an in particular compact device is obtained.

According to an exemplary embodiment of the invention, the detection apparatus can be configured to establish a fluidic path out of the further pressure vessel and the further measuring cell as a reference measurement path for a measurement path out of the pressure vessel and the measuring cell. The accuracy and reliability of the actual main measurement can be improved by such a reference or a calibration path.

According to an exemplary embodiment of the invention, a fluidic path out of the further pressure vessel and the further measuring cell can be configured as an additional measurement path for determining information being indicative for a zeta potential for characterising the interface between the further solid phase and the further liquid phase. A measurement of a plurality of samples can be carried out in a narrow space and with easily comparable conditions in parallel or sequentially using a compact device, which can share at least a portion of the components thereof for a plurality of measurement tasks.

According to an exemplary embodiment of the invention, the detection apparatus can be configured for detecting the information being indicative for the zeta potential whilst carrying out a baseline correction, in particular a correction of a baseline, which changes over time. Preferably, voltage values can be modelled in the case of a continuously changed pressure profile (i.e. the streaming potential at the applied pressure) and the baseline (asymmetry potential at differential pressure zero) by means of a modelling function (for example by means of a polynomial function, in particular second order). The temporal drift of the baseline can then be subtracted from the temporal curve of the streaming potential at decreasing pressure difference. With such a baseline correction, the accuracy and reliability of the determined measurement results can be further improved.

According to an exemplary embodiment of the invention, the baseline correction can take place, taking account of an asymmetry potential of an input electrode at an input of the measuring cell and an output electrode at an output of the measuring cell. In particular, the baseline correction can take place, taking account of a temporal change of the asymmetry potential with regard to a relationship between a streaming potential or a streaming current on the one hand and a differential pressure on the other hand. According to an exemplary embodiment of the invention, the detection apparatus can be configured for detecting a base signal, which is independent of the solid phase and the liquid phase and in particular based on an asymmetry potential of an input electrode at an input of the measuring cell and an output electrode at an output of the measuring cell, during the loading the pressure vessel with the pressure profile.

Taking account of the asymmetry potential of the measuring electrodes (also termed baseline correction) and the temporal change thereof in the evaluation of the pressure ramps (relationship between streaming potential or streaming current and differential pressure) is advantageous for a highly precise and unique interpretation in the following scenarios in particular:
  measured pressure ramps at high ionic strength;
  measured pressure ramps in the direct vicinity of the isoelectric point (independently of the chosen ionic strength);
  measured pressure ramps on metallic material surfaces; and also
  change of streaming potential or streaming current during the adsorption or desorption processes.

In particular in the mentioned critical scenarios, taking account of a baseline correction by means of the described device leads to an accurate determination of the zeta potential (i.e. with a very small measurement error). In other scenarios, by contrast, the baseline correction can also be omitted.

In particular, in the listed examples, the value of the actual measurement signal of streaming potential or streaming current can occasionally be smaller than that of the asymmetry potential (baseline). In the case of a temporally constant baseline, a correction is not necessary, in order to obtain a plausible result (slope of the pressure ramp) in spite of these unfavourable conditions (measurement signal smaller than base signal). However, the mentioned influencing values (in particular polarisability of the electrodes, flow at the electrode surfaces, thermal drift of the electronics, influence of adsorbate) lead to an unreproducible temporal change of this base signal under unfavourable conditions. In addition to the streaming potential or current during the pressure difference, the knowledge (for example based on corresponding measurements) of the base signal is very advantageous during the measurement time.

Advantages of a device or a method according to exemplary embodiments of the invention first lie in the fact that a compressed gas volume expands independently and therefore no pressure pulses (and consequently no measurement artefacts, for example due to a pump or due to regulation of a constantly applied external gas pressure) are generated during the measurement. Second, under unfavourable basic conditions, thus optionally, precisely the combination of such a device or such a method with a parallel measurement of streaming potential or current and the temporal change of the base signal also allows the applicability of the method under measurement conditions, which lead to extremely small measured values (see the above mentioned fields of application).

Exemplary embodiments, in particular with baseline correction, can therefore be applied in particular advantageously in the following use cases:
  determining the information being indicative for the zeta potential at high ionic strength, in particular at an ionic strength of at least approximately 0.001 mol/l, furthermore in particular at an ionic strength of at least approximately 0.1 mol/l
  determining the information being indicative for the zeta potential during an adsorption process or during a desorption process (in particular at the solid phase)
  determining the information being indicative for the zeta potential at a metallic material surface (in particular the solid phase)
  determining the information being indicative for the zeta potential in the direct vicinity of the isoelectric point (i.e. the pH value of the liquid phase, in which positive charges and negative charges are compensated), in particular at a deviation of the pH value of at most five percent from the isoelectric point.

According to an exemplary embodiment, the pressure loading apparatus for loading the pressure vessel with a pressure profile can be configured in such a manner that a pressure difference between an initial pressure value at the pressure vessel and an initial pressure value at the storage vessel is greater than approximately one atmosphere, in particular greater than approximately 2 bar, furthermore is between approximately 5 bar and approximately 10 bar in particular. Clearly, the pressure loading apparatus preferably applies an overpressure to the pressure vessel (instead of applying an underpressure). As a result, very high differential pressures can also be obtained and thus the range of measurements that can be carried out (in particular with regards to measurable materials) can be expanded.

BRIEF DESCRIPTION OF THE DRAWINGS

Exemplary embodiments of the present invention are described in detail in the following with reference to the following figures.

Identical or similar components in different figures are provided with the identical reference numbers.

DETAILED DESCRIPTION OF EXEMPLARY EMBODIMENTS

Before exemplary embodiments of the invention are described with reference to the figures, a few general aspects of the invention should also be explained:

In the case of a pressure ramp measurement, the streaming potential $U_{str}(\Delta p)$ is measured simultaneously to a continuously increasing pressure difference and the streaming potential coefficient $dU_{str}/d\Delta p$ in Equation 2 is determined as the slope of the linear regression of the measurement points. The pressure ramp measurement has the advantage compared to a pressure stage measurement of the larger number of individual measurement points (increase of the quality of the measurement result) and the substantially shorter measurement time.

The measurement of the streaming potential and the streaming current according to conventional measuring methods is limited to the determination of the zeta potential at low ionic strengths (I<0.1 mol/l). With increasing ionic strength, the measurement signal of the streaming potential (approximately double-exponential fall) and also the streaming current (approximately exponential fall) is reduced. Thus, the streaming potential arising approaches the order of magnitude of the asymmetry potential for a certain pressure difference. In addition to the contributions to electrode polarisation, further effects occur in this size range, which are to be taken into account for the measurement of small signals:

Such an effect is the temporal dependency of the electrode polarisation. For measurements of the streaming potential and the streaming current in particular in the presence of high ionic strengths (I≥0.1 mol/l), it is no longer readily permissible to assume a temporally stable asymmetry potential on the basis of electrode polarisation. Rather, often it can be observed that temporally changing polarisation effects also affect the stability of the measurement signal. The influence of electrically conductive materials, for example metals, on the asymmetry potential and the temporal instability thereof should likewise be taken into account.

Figure 7:
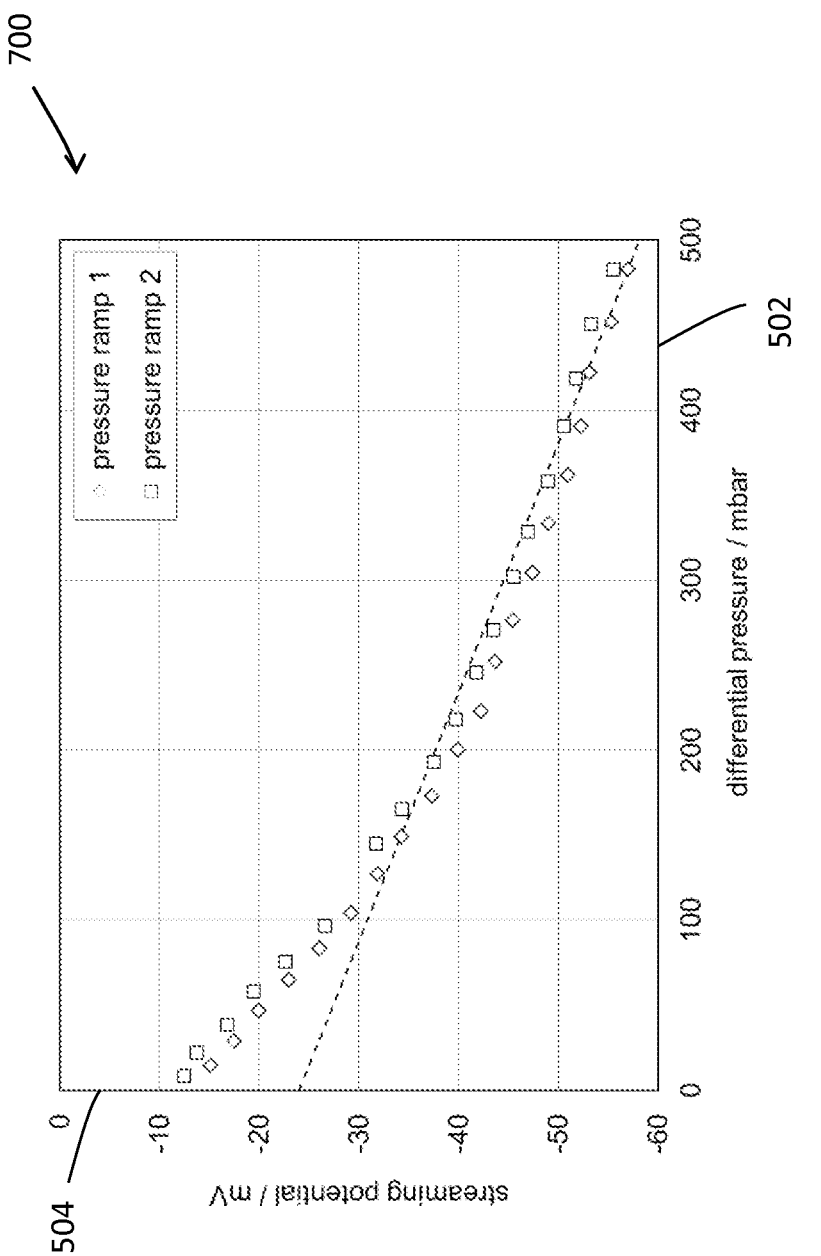
FIG. 7 shows a graph, which, for the example of a pressure ramp measurement for a conductive sample in the presence of a 0.001 mol/l KCl solution, shows a dependency between a pressure difference and the streaming potential.

FIG. 7 shows the example of a pressure ramp measurement for a conductive sample in the presence of a 0.001 mol/l KCl solution. In spite of the low ionic strength (I=0.001 mol/l), a significant deviation from the expected linear relationship between streaming potential and differential pressure can be seen here. The cause lies in a temporal change of the asymmetry potential (baseline) during the pressure ramp measurement.

The flow-dependent electrode polarisation is also to be taken into account. For high ionic strength and therefore for small measured values of the streaming potential and the streaming current, polarisation effects are observed in addition to contributions to electrode polarisation, which polarisation effects are flow-dependent (cf. Vinogradov J, Jaafar M Z, Jackson M D (2010) "Measurement of streaming potential coupling coefficient in sandstones saturated with natural and artificial brines at high salinity", J Geophys Res 115: B1 2204). A solution for avoiding this effect is the use of external electrodes, which are connected via a salt bridge to the electrolyte solution used for the measurement of streaming potential and streaming current. The disadvantage of this method lies in the reduced sensitivity and temporal response time of the external measuring electrodes.

Effects of the electronics also contribute. In the presence of electrolyte solutions with high ionic strength, the values of the streaming potential and the streaming current approach the resolution limit of the corresponding measurement ranges. The signal/noise ratio is therefore also co-determined by electronic drift, for example on the basis of temperature fluctuations.

According to exemplary embodiments, a device and a method can be provided for determining the zeta potential at solid surfaces with a correction of the baseline. A correction of the described influences is advantageous for the correct measurement of the streaming potential and streaming current, in particular in the case of high ionic strength.

On the one hand, according to an exemplary embodiment, pulsation effects are taken into account or suppressed. The use of a mechanical pump for applying the pressure difference for measuring one or a plurality of pressure stages and pressure ramps leads to pulsations in the liquid flow and therefore in the pressure difference, which directly affect the signal of the streaming potential and the streaming current. For the determination of the zeta potential from measurements of the streaming potential and streaming current, a pulsation-free application of the pressure difference is therefore very advantageous for the entire field of use of the ionic strength, in particular in the case of high ionic strength, however. For the compensation of the time-dependent influences of electrode polarisation and other drift occurrences on voltage and current values in the stationary state (baseline), a pulsation-free and temporally continuous change of the pressure difference is enabled.

Figure 1:
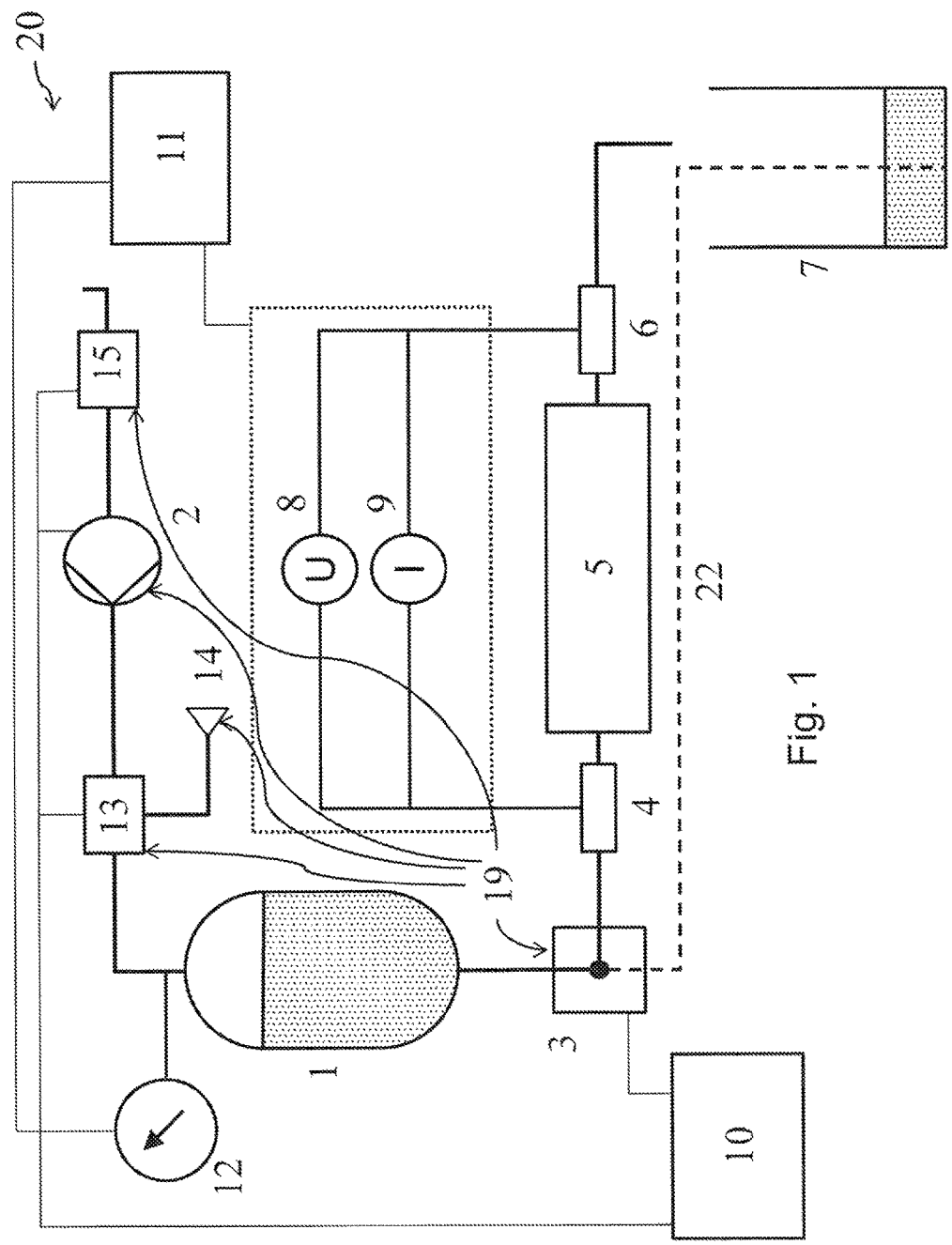
FIG. 1 and FIG. 2 show devices according to exemplary embodiments of the invention, for determining a zeta potential of a sample with a solid phase and with a liquid phase, in order to obtain information about this sample, in particular information about the interface or an interaction between the solid phase and the liquid phase.

FIG. 1 shows a device 20 according to an exemplary embodiment of the invention for determining information being indicative for a zeta potential, in order to characterise the interface between a solid phase (as sample to be investigated) and a liquid phase (in particular a test liquid).

The device 20 comprises a pressure vessel 1, in which the liquid phase (that is to say a liquid to be investigated) can be accommodated. The pressure vessel 1 is fluid-connected upstream thereof to a valve 13 and to a pressure measuring unit 12 and is connected downstream thereof to a switching element 3 (configured as a further fluid valve). Otherwise, the pressure vessel 1 is hermetically sealed or pressure-decoupled with respect to the environment, so that a pressure different from the surrounding atmospheric pressure can prevail or be set in the interior of the pressure vessel 1.

Furthermore, the device 20 has a measuring cell 5, which is arranged downstream of the pressure vessel 1 with respect to a normal flow direction of the liquid and can be brought into fluid communication with the pressure vessel 1 if the switching element 3 is switched by a control apparatus 10 in an operating state permitting this fluid communication, which can also be termed the passage state. By contrast, if the control apparatus 10 switches the switching element 3 into a blocking state, a fluid communication between the pressure vessel 1 and the measuring cell 5 is temporarily rendered impossible. The solid phase (i.e. the solid to be investigated, the interaction of which with the liquid to be investigated should be analysed in particular) can be or is accommodated in the measuring cell 5.

An open, overpressure-free storage vessel 7, which is at atmospheric or ambient pressure, is arranged downstream of the measuring cell 5. As the storage vessel 7 is in fluid communication with the measuring cell 5, the liquid phase can, after flowing through the measuring cell 5, be let out of the same and captured or accommodated in the storage vessel 7. The storage vessel 7 is an open container and therefore connected to the surrounding atmosphere.

The device 20 furthermore has a pressure loading apparatus 19, which is formed by a plurality of mutually interacting components. The pressure loading apparatus 19 is configured for loading the pressure vessel 1 with a predeterminable pressure profile with a temporally continuous pressure change. This means that a temporally changeable pressure value, which is controlled by means of the control apparatus 10 (for example a processor or a part of a processor) is applied to the pressure vessel 1 and consequently to the measuring cell 5, which pressure value for example continuously or steadily drops (for example drops linearly over time) starting from an initial value during the measurement for detecting the information being indicative for the zeta potential. Under the influence of this temporally changeable and continuously reducible pressure profile, liquid phase is continuously conveyed out of the pressure vessel 1 through the measuring cell 5 into the storage vessel 7. Descriptively speaking, the pressure in the pressure vessel 1 drops continuously over time, whilst the pressure in the storage vessel 7 constantly remains at atmospheric pressure. Measurement artefacts are prevented or eliminated in that the pressure loading apparatus 19 provides a pressure profile with a pulsation-free pressure change to the measuring cell 5, so that even direct and undesired changes in the streaming potential or streaming current in the liquid flow are prevented or eliminated. This increases the measurement accuracy and the reproducibility of the measurement, as disruptive influences can be compensated or at least reduced considerably. The pressure loading apparatus 19 is set up to load a gas space above the liquid phase in the pressure vessel 1 with a compressed gas cushion, which presses onto the liquid surface, in order to, as a consequence, generate the pressure profile with a continuous drop in the pressure. For this purpose, the pressure loading apparatus 19 comprises a pressure generation unit (realised in the exemplary embodiment shown by a pump 2 (for example a membrane pump) downstream of a further fluid valve 15 or a gas pressure supply 14 (for example a nitrogen gas bottle)) for generating pressure. The switching element 3 also forms part of the pressure loading apparatus 19 and can be switched by means of the control apparatus 10 in that by means of the switching of the switching element 3 for fluid coupling of the pressure generation unit 2 or 14 with the measuring cell 5, the measuring cell 5 is loaded with the liquid phase in accordance with the controlled predetermined pressure profile.

The device 20 furthermore comprises the pressure measuring unit 12 for detecting the pressure curve according to the loaded pressure profile directly upstream of the pressure vessel 1. A detected pressure value is transmitted by the pressure measuring unit 12 of the control apparatus 10 and a detection apparatus 11. The switching element 3 is then switched in a manner controlled by the control apparatus 10 such that the switching element 3 activates the fluid connection between the pressure vessel 1 and the measuring cell 5 in the event of exceeding of a predeterminable pressure value (which can correspond to the initial value of the pressure profile to be applied), which exceeding is detected by means of the pressure measuring unit 12. After this switching of the switching element 3, this generated pressure is used in order to transfer the liquid phase out of the pressure vessel 1, through the measuring cell 5 into the storage vessel 7, which is continuously at atmospheric pressure. As a result, the differential pressure between pressure vessel 1 and storage vessel 7 or between an input and an output of the measuring cell 5 is reduced in a manner that is continuous and pulsation-free.

A detection apparatus 11 (for example a processor or a part of a processor) is configured for detecting the information being indicative for the zeta potential at the measuring cell 5 during the loading of the pressure vessel 1 with the pressure profile. The detection apparatus 11 is configured for detecting the information being indicative for the zeta potential on the basis of a current measurement (see reference number 9 in FIG. 1) and on the basis of a voltage measurement (see reference number 8 in FIG. 1) at the measuring cell 5. To this end, the device 20 has an input electrode 4 at an input of the measuring cell 5 and an output electrode 6 at an output of the measuring cell 5, the detection apparatus 11 being arranged for detecting signals or measured values between the input electrode 4 and the output electrode 6. The input electrode 4 is arranged for interacting with the liquid phase at the input of the measuring cell 5 and the output electrode 6 is arranged for interacting with the liquid phase at the output of the measuring cell 5. The detection apparatus 11 optionally also detects information being indicative for an electrical resistance of the solid phase and the liquid phase in the measuring cell 5 by means of the input electrode 4 and by means of the output electrode 6. On the basis of this information, it is possible to determine whether undesired gas bubbles, which would distort the measurement of the zeta potential, are located in the measuring cell 5. This information can also be called upon in order to determine a contribution of the solid phase to the total electrical conductivity.

The device 20 furthermore comprises a liquid phase return mechanism for returning liquid phase from the storage vessel 7 to the pressure vessel 1. The liquid phase return mechanism is formed by a fluid line 22, the one end of which dips into the liquid phase, which is accommodated in the storage vessel 7 and already measured, and the other end of which can be brought into fluid connection with the pressure vessel 1 by means of the switching element 3. The switching element 3 is therefore arranged in the fluid path constituted by the fluid line 22, in which liquid phase can be returned from the storage vessel 7 to the pressure vessel 1 by means of the liquid phase return mechanism. The pump 2 can apply the conveying power for returning the liquid and to this end, compared to previous, convey the liquid in the reverse direction.

The device 20 shown in FIG. 1 is configured for a pulsation-free change of the pressure difference with simultaneous measurement of the streaming potential and the streaming current. In the pressure vessel 1, the pressure in the gas chamber above the liquid is increased using the pump 2, for example a membrane pump, or the gas pressure supply 14, for example a nitrogen gas bottle. The generated pressure is measured via the pressure measuring unit 12. Subsequently, the switching element 3 realised as a valve opens and the liquid flows through or past the input electrode 4 into the measuring cell 5. The opening and closing of the switching element 3 and the control or regulation of the pump 2 takes place via the control apparatus 10. The solid sample in the measuring cell 5 is fastened at appropriate sample supports in such a manner that a flow channel in the form of a capillary, for example with a rectangular cross-sectional area, is formed from the sample material. After the measuring cell 5, the liquid flows through or past the output electrode 6 and is captured in the storage vessel 7. During this process, the differential pressure (i.e. gas pressure in the pressure vessel 1 versus atmospheric pressure) drops successively and a streaming potential or a streaming current are generated during the passage of the liquid through the flow channel in the measuring cell 5. The streaming potential is measured as a voltage value between the input electrode 4 and the output electrode 6 across an electric circuit (see reference number 8). The streaming current is measured as a current value between the input electrode 4 and the output electrode 6 across a further electric circuit (see reference number 9). The measured values are transmitted to the evaluation unit or detection apparatus 11 for determining the zeta potential.

The device 20 described in FIG. 1 can also be used to transfer liquid out of the storage vessel 7 into the pressure vessel 1 with the aid of the pump 2, for example a membrane pump, by a corresponding switching of the switching element 3.

FIG. 1 additionally shows a valve arrangement, which is formed from the valves 13, 15, for loading pressure in the pressure vessel 1, by means of the pump 2 or the external gas pressure supply 14 and generating overpressure for transferring or returning liquid out of the storage vessel 7 into the pressure vessel 1 (i.e. by means of suction). The control or regulation of the valves 13, 15, which can be formed for example as a plurality of 2-way valves or 3-way valves, likewise takes place by means of the control apparatus 10.

The input electrode 4 and the output electrode 6 are also used to measure the electrical resistance in the flow channel of the measuring cell 5. The resistance is predominantly used for controlling the air-bubble-free filling of the measuring cell 5 and in particular the flow channel, but is also used to determine the contribution of the solid sample to the total electrical conductivity in the flow channel. The knowledge of the actual total conductivity in the flow channel enables the correction of the zeta potential calculated according to the above Equation 2 in the case of ionically or electronically conductive solid samples.

The pressure loading of the measurement solution with a compressed gas cushion and the continuous drop of the pressure after the switching of the switching element 3 enables a pulsation-free change of the pressure difference. The pulsation-free application of the pressure difference is advantageous in particular in the case of a temporally changing pressure difference, as pulsations in the liquid flow lead to direct and undesired changes in the streaming potential or streaming current. These fluctuations can lead to a systematic error in the calculation of the zeta potential.

A baseline correction can significantly improve the measurement accuracy in certain scenarios in the case of the device 20 according to FIG. 1. For this purpose, the valve 3 can be switched alternately between its valve position permitting a fluid connection and its valve position preventing a fluid connection, in order to detect a baseline signal (in particular a number of times) in the valve position preventing the fluid connection and thus to correct the measurement in the valve position permitting the fluid connection.

Figure 2:
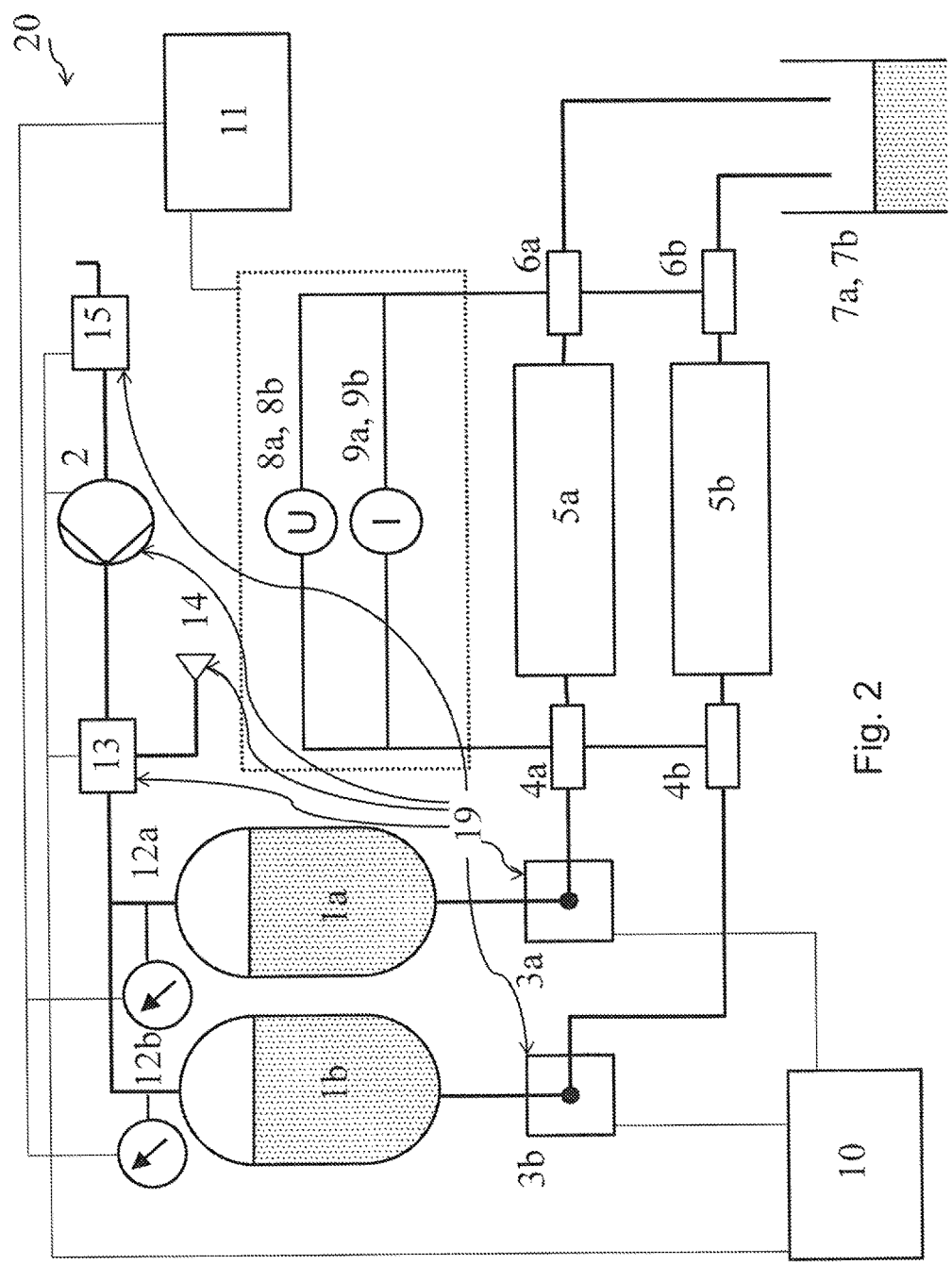

FIG. 2 shows a device 20 for determining information being indicative for a zeta potential at the interface between a solid phase and a liquid phase according to a different exemplary embodiment of the invention. The device 20 shown in FIG. 2 duplicates a few of the components shown in FIG. 1, wherein for better differentiation, the reference numbers used in FIG. 1 are labelled with the additional letter "a" in FIG. 2 (for example pressure vessel is corresponds to the pressure vessel 1 according to FIG. 1, etc.).

The device 20 furthermore comprises a further pressure vessel 1b, in which further liquid phase can be accommodated. Furthermore, the device 20 according to FIG. 2 additionally comprises a further measuring cell 5b, which is arranged downstream of and in fluid communication with the further pressure vessel 1b and in which the further solid phase can be accommodated. The pressure loading apparatus 19 is configured in such a manner for also loading the further pressure vessel 1b with a pressure profile with a temporally continuous pressure change that, as a result, further liquid phase can be conveyed out of the further pressure vessel 1b through the further measuring cell 5b. The detection apparatus 11 can additionally be constructed for detecting information being indicative for the zeta potential at the further measuring cell 5b during the loading of the further pressure vessel 1b with the pressure profile.

According to an alternative, the detection apparatus 11 is constructed to use a fluid path out of the further pressure vessel 1b and the further measuring cell 5b as reference measurement path for a measurement path out of the pressure vessel is and the measuring cell 5a.

According to another alternative, a fluid path out of the further pressure vessel 1b and the further measuring cell 5b can be constructed as an additional measurement path for determining information being indicative for a zeta potential at the interface between the further solid phase and the further liquid phase.

FIG. 2 shows the above-described construction with an additional measurement branch. The measurement branch is formed from the further pressure vessel 1b, a further valve as further switching element 3b, the further measuring cell 5b, two further electrodes 4b, 6b (that is to say a further input electrode and a further output electrode) and a further pressure measuring unit 12b. The additional measurement branch is used for example for measuring a reference sample, wherein the two pressure vessels 1a and 1b are filled with solutions that are different from one another and therefore different solutions flow through or flow around identical samples in the measuring cells 5a and 5b, in order to determine the different adsorption behaviour at the sample. In this case, the basic solution and the measurement solution are located in separate pressure vessels 1a, 1b. The measured pressures of the two pressure measuring units 12a, 12b are delivered to the evaluation unit or detection apparatus 11 for determining the zeta potential.

In a manner analogous to that described above, the two different solutions can be captured in two separate storage vessels 7a, 7b and conveyed back to the respective pressure vessels 1a or 1b by means of suitable switching of the respective valves (see reference numbers 3a, 3b, 13, 15).

Furthermore, two different samples can be measured using the same measurement solution. For example, an untreated reference sample (measuring cell 5a) can thus be measured in parallel with a surface-modified sample (measuring cell 5b) and the measurement results are compared directly. Here, it is in turn possible to transport the measurement solution from the storage vessel 7 (respectively 7a, 7b) via a suitable control or regulation of the respective valves (see reference numbers 3a, 3b, 13, 15) back into the pressure vessel 1 (or 1a, 1b).

The control apparatus 10 in this case controls or regulates the valves (see reference numbers 3a, 3b, 13 and 15) and the pump 2 depending on the measurement principle chosen. The described device 20 for pulsation-free change of the pressure difference enables a continuous measurement of this change and the associated change of the streaming potential or streaming current.

Figure 3:
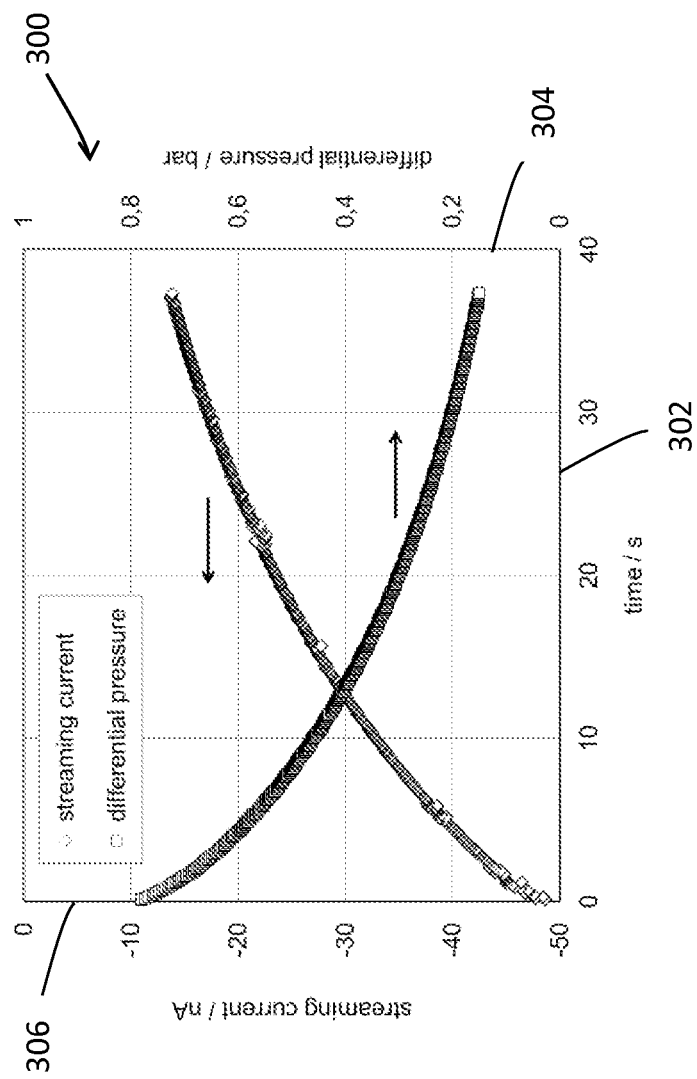
FIG. 3 shows a graph, which as an example shows a measurement of streaming current in the pressure range 150-800 mbar and shows a dependence between the time, a pressure difference and the streaming current according to exemplary embodiments of the invention.

FIG. 3 shows a graph 300, which as an example shows a measurement of streaming current in the pressure range 150-800 mbar and shows a dependence between the time (see abscissa 302), a pressure difference (see first ordinate 304) and the streaming current (see second ordinate 306) according to exemplary embodiments of the invention. FIG. 3 shows the drop of the differential pressure and the negative streaming current after pressure loading of the pressure vessel 1. The linear correlation of streaming current and differential pressure (373 measurement points) give the streaming current coefficient $dI_{str}/d\Delta p=-63.3$ nA/bar. For a precise assignment of differential pressure and associated streaming potential or streaming current, the simultaneous measurement of these parameters is important. The measurement takes place in the sub-second range, preferably every 100 ms. The streaming current coefficient in the example in FIG. 3 results from the linear regression of the dependence of the streaming current on the differential pressure.

At a higher ionic strength, the signal/noise ratio is reduced. The temporal change of the voltage or current value under stationary conditions ($\Delta p=0$ bar) leads to a deviation in the linearity of the relationship between streaming potential or streaming current and the differential pressure. The continuous shift of the baseline, caused by the above-described effects of electrode polarisation and electronic drift occurrences, and the influence thereof on the measurement signal (streaming potential or streaming current) are recorded by successive measurements of voltage or current with an applied pressure difference $\Delta p=0$ bar. In this case, the applied pressure difference continuously changes from high to low pressure difference during the cycles of the measurements of streaming potential and streaming current.

Figure 4:
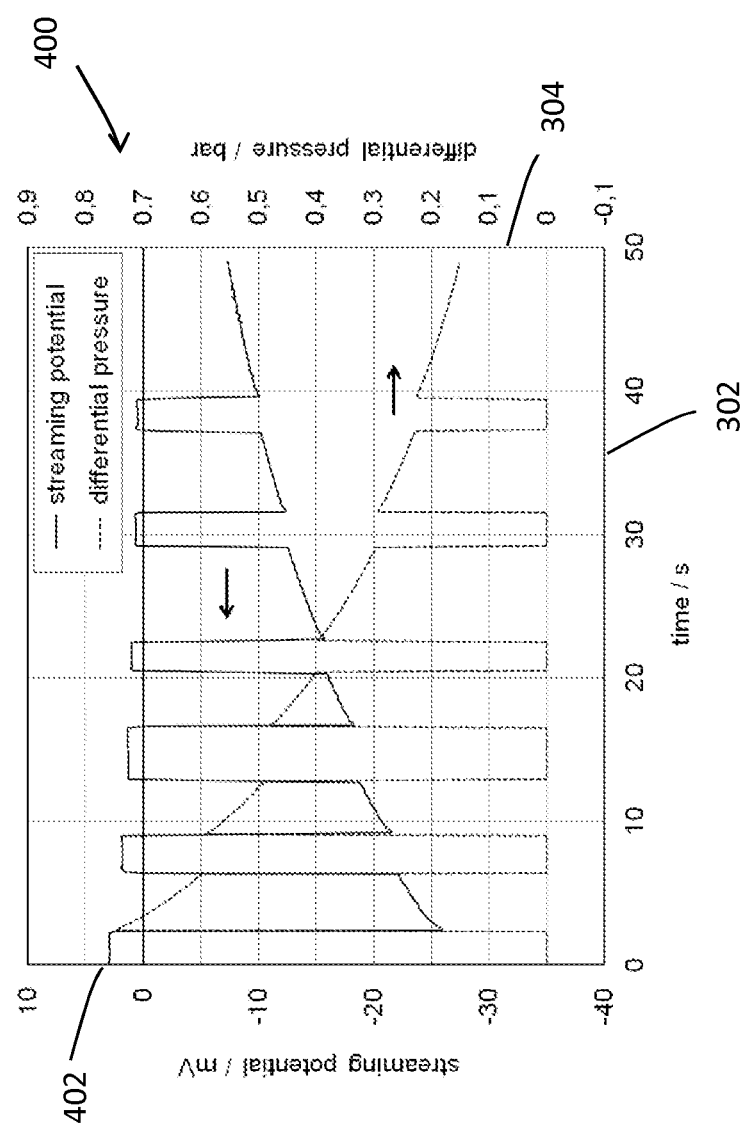
FIG. 4 shows a graph, which as an example shows the measurement of the streaming potential during the continuous drop of the differential pressure and the series-connected measurement of the temporal change of the asymmetry potential, and shows a dependence between the time, a pressure difference and the streaming potential according to exemplary embodiments of the invention.

FIG. 4 shows a graph 400 as an example for the measurement of the streaming potential during the continuous drop of the differential pressure and the series-connected measurement of the temporal change of the asymmetry potential. The graph 400 shows a dependence between the time, a pressure difference and the streaming potential (see additional ordinate 402) according to exemplary embodiments of the invention. The method for correcting the baseline is clarified in that the streaming potential (in the case of an applied differential pressure) or the asymmetry potential (when $\Delta p=0$ bar) are plotted against the differential pressure (FIG. 5: pressure data for the stationary state, i.e. $\Delta p=0$, are not shown).

Figure 5:
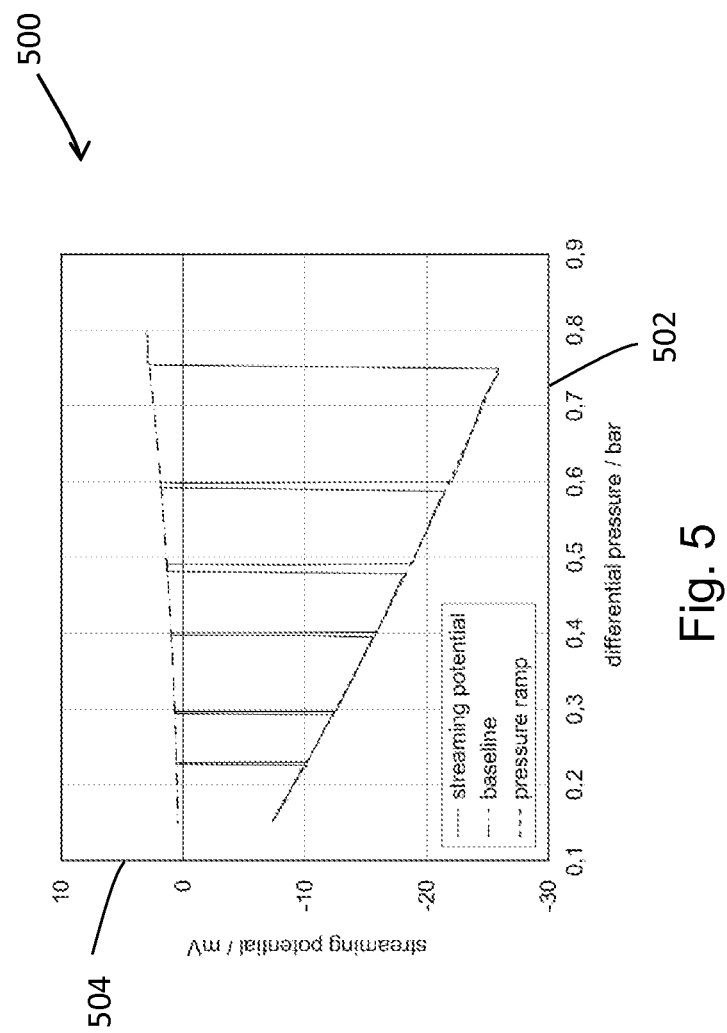
FIG. 5 and FIG. 6 show graphs, which clarify a method for correcting a baseline according to exemplary embodiments of the invention in that the streaming potential (with an applied differential pressure) or the asymmetry potential (for $\Delta p=0$ bar) is plotted against the differential pressure.

FIG. 5 shows a graph 500, which clarifies a method for correcting a baseline according to an exemplary embodiment of the invention in that the streaming potential (with an applied differential pressure) or the asymmetry potential (for $\Delta p=0$ bar) along an ordinate 504 is plotted against the differential pressure shown on the abscissa 502. FIG. 5 therefore illustrates the streaming potential as a function of the differential pressure. The streaming potential at $\Delta p=0$ bar (pressure data not shown) corresponds to the asymmetry potential (baseline). The voltage values of the baseline and the pressure ramp are described by suitable functions, preferably by second order polynomials, which are used for correcting the baseline.

Figure 6:
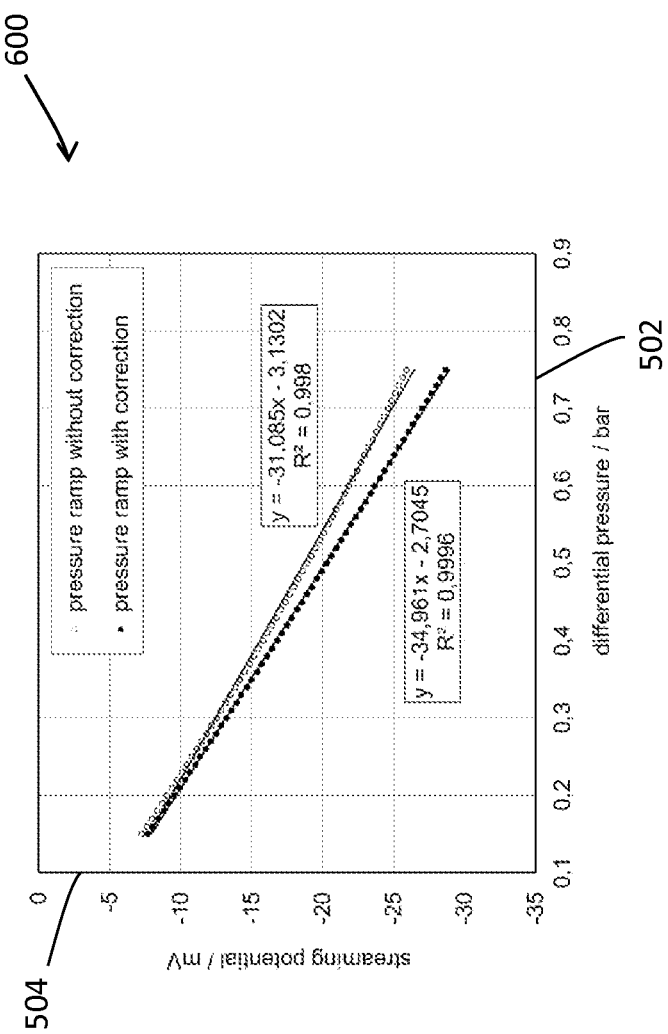

FIG. 6 shows a graph 600, which clarifies a method for correcting a baseline according to an exemplary embodiment of the invention in that the streaming potential (with an applied differential pressure) or the asymmetry potential (for $\Delta p=0$ bar) along the ordinate 504 is plotted against the differential pressure shown on the abscissa 502. FIG. 6 therefore shows a comparison of the pressure ramp (streaming potentials versus differential pressure) with a baseline correction ($dU_{str}/d\Delta p=-34.96$ mV/bar) with the pressure ramp without baseline correction ($dU_{str}/d\Delta p=-31.09$ mV/bar). The error in the streaming potential coefficient (gradient) and therefore in the zeta potential is 12% (the data from FIG. 4 and FIG. 5 having been used).

The voltage values of the pressure ramp (streaming potential in the case of applied pressure) and the baseline (asymmetry potential when $\Delta p=0$ bar) are described by suitable functions, preferably by a 2nd order polynomial function. The temporal drift of the baseline is subtracted from the temporal curve of the streaming potential with simultaneously decreasing pressure difference. Without baseline correction, a streaming potential coefficient $dU_{str}/d\Delta p=-31.085$ mV/bar and a linear regression coefficient $r^2=0.998$ result from the measured values of streaming potential and differential pressure in FIG. 4 and FIG. 5. With the aid of the method of baseline correction described here, one obtains the values $dU_{str}/d\Delta p=-34.961$ mV/bar and $r^2=0.9996$ (FIG. 6).

FIG. 7 shows a graph 700, which, for the example of a pressure ramp measurement for a conductive sample in the presence of a 0.001 mol/l KCl solution, shows a dependence between a pressure difference and the streaming potential. The linearity of the relationship between streaming potential and differential pressure without baseline correction is seen as insufficient in certain scenarios (measurement points in FIG. 7), in which a very high measurement accuracy is desired. The dashed line shows the correct gradient after the correction of the baseline, as a result of which a more greatly improved measurement accuracy can be obtained.

Use examples according to exemplary embodiments are explained in the following.

The isoelectric point (IEP) is defined as the pH value of an aqueous solution, at which the zeta potential assumes the value 0 mV. Independently of the ionic strength of the electrolyte solution, the streaming potential and streaming current values in the direct vicinity of the IEP are therefore very low. A temporal change of the asymmetry potential of the electrodes therefore influences the quality of the measurements of streaming potential and streaming current even at low ionic strength. At higher ionic strengths, the electrode polarisation contributes to the temporal instability of the baseline owing to the electrolyte concentration and other drift occurrences.

The determination of the IEP is in particular critical in the case of materials, which, due to the porosity or swellability thereof, contribute considerably to the electrical conductivity in the flow channel of the measuring cell, and also in the case of materials which have their IEP in the low pH range. As examples for the determination of the IEP under these aggravating conditions, mention may be made of cellulose fibres (strong swellability) or the proof of sulphonic acid groups (IEP at pH<2) on correspondingly modified polymer surfaces.

A measurement at high ionic strength becomes possible. With increasing electrolyte concentration (ionic strength), the polarisability of electrodes increases. Without correction of the baseline and the temporal change thereof, a measurement of streaming potential and streaming current often does not lead to sensible results at ionic strengths of I>0.1 mol/l.

One example is the characterisation of polymer membranes for nanofiltration and reverse osmosis, the zeta potential of which should be determined in the presence of high ionic strength, which corresponds to the salinity of seawater (I>0.5-0.7 mol/l). A further example is the measurement of the streaming potential and streaming current at surfaces of steel or titanium alloys in the presence of physiological buffer solutions (I>0.15 mol/l).

Adsorption processes can also be measured. The described device for a pulsation-free change of the pressure difference with simultaneous measurement of the streaming potential and streaming current and the likewise described method of baseline correction are suitable for measuring adsorption processes of substances dissolved in liquid, such as for example tensides, proteins and other polyelectrolytes, and also nanoparticles suspended in liquid, at solid surfaces of different size and shape. The introduction of these substances, termed adsorbate in the following, into the measurement solution and the measurement of the streaming potential or streaming current in changing concentration of adsorbate in the flow channel may lead to a further polarisation effect of the measuring electrodes. The significance of this effect is dependent on the type and concentration of the adsorbate and the ionic strength of the electrolyte solution, out of which the adsorption on the solid surface takes place. The measurement of adsorption processes is essentially desired at high ionic strength, for example in the presence of physiological buffer solutions (I>0.15 mol/l). Complex adsorbates, for example proteins, are adsorbed at least temporarily at the surface of the measuring electrodes and therefore change the asymmetry potential (baseline). A serial measurement of streaming potential in the case of an applied pressure difference (as indicator of the adsorption process) and the asymmetry potential when Δp=0 bar (baseline) is therefore advantageous for a reasonable analysis of the adsorption process.

Use examples are the analysis of hair samples in the presence of emulsions (e.g. shampoo, conditioner), the characterisation of the cleaning efficiency of a dishwashing detergent on glass surfaces or the interaction of detergent and fabric softener with textile fabric, and the above-mentioned interaction of proteins with the surface of biomaterials (metals, ceramics, polymers, etc.).

In addition, it is to be pointed out that "comprising" does not exclude any different elements or steps and "a" or "an" does not exclude a multiplicity. Furthermore, it may be pointed out that features or steps, which have been described with reference to one of the above exemplary embodiments, can also be used in combination with other features or steps of other above-described exemplary embodiments. Reference numbers in the claims are not to be seen as limiting.

What is claimed is:

1. A method for determining information being indicative for a zeta potential for characterising an interface between a solid phase and a liquid phase, wherein the method comprises:
    accommodating the liquid phase in a pressure vessel;
    accommodating the solid phase in a measuring cell, which is arranged downstream of and such that it can be brought into fluid communication with the pressure vessel;
    arranging a storage vessel downstream of and in fluid communication with the measuring cell;
    loading the pressure vessel with a pressure profile with a temporally continuous pressure change in such a manner that as a result liquid phase can be conveyed out of the pressure vessel through the measuring cell into the storage vessel, wherein the interior of the pressure vessel is pressure-decoupled from the environment when the liquid phase flows out of the pressure vessel, and wherein the pressure drops continuously when the liquid phase flows out of the pressure vessel; and
    determining the information being indicative for the zeta potential at the measuring cell during the loading of the pressure vessel with the pressure profile.

2. The method as set forth in claim 1, wherein determining the information being indicative for the zeta potential is carried out at high ionic strength, and/or during an adsorption process or during a desorption process, and/or at a metallic material surface, and/or in the direct vicinity of the isoelectric point.

3. The method as set forth in claim 1, wherein the measuring cell is provided with a pressure profile with a pulsation-free pressure change.

4. The method as set forth in claim 1, wherein the information being indicative for the zeta potential is determined whilst carrying out a baseline correction which changes over time.

5. The method as set forth in claim 1, wherein a base signal, which is independent of the solid phase and the liquid phase is determined during the loading of the pressure vessel with the pressure profile; and/or wherein during the pressure change, there is changed in an alternating manner between an operating mode permitting a fluid connection between the pressure vessel and the measuring cell and an operating mode preventing a fluid connection between the pressure vessel and the measuring cell, in order to detect, in the operating mode preventing the fluid connection, a baseline signal and thereby to correct a measurement signal detected in the operating mode permitting the fluid connection.

6. A device for determining information indicative for a zeta potential, for characterising an interface between a solid phase and a liquid phase, wherein the device comprises:
  a pressure vessel, in which the liquid phase can be accommodated;
  a measuring cell, which is arranged downstream of the pressure vessel and such that it can be brought into fluid communication with the pressure vessel and in which the solid phase can be accommodated;
  a storage vessel which is arranged downstream of and in fluid communication with the measuring cell;
  a pressure loading apparatus, which is configured for loading the pressure vessel with a pressure profile with a temporally continuous pressure change in such a manner that as a result, liquid phase can be conveyed out of the pressure vessel through the measuring cell into the storage vessel, wherein the interior of the pressure vessel is pressure-decoupled from the environment when the liquid phase flows out of the pressure vessel, and wherein the pressure drops continuously when the liquid phase flows out of the pressure vessel; and
  a detection apparatus for detecting the information being indicative for the zeta potential at the measuring cell during the loading of the pressure vessel with the pressure profile.

7. The device as set forth in claim 6, wherein the pressure loading apparatus is configured to provide a pressure profile with a pulsation-free pressure change to the measuring cell.

8. The device as set forth in claim 6, wherein the pressure loading apparatus is configured to load a gas chamber above the liquid phase in the pressure vessel with a compressed gas cushion in order to, as a consequence, generate the pressure profile with the continuous drop of the pressure.

9. The device as set forth in claim 6, wherein the pressure loading apparatus comprises a pressure generation unit for generating pressure in the pressure vessel and a switching element, said switching element fluidly coupling the pressure vessel with the measuring cell, the measuring cell receiving the liquid phase in accordance with the pressure profile.

10. The device as set forth in claim 9, wherein the switching element is arranged between the pressure vessel and the measuring cell.

11. The device as set forth in claim 9, comprising a pressure measuring unit for detecting a pressure.

12. The device as set forth in claim 11, wherein the switching element can be switched in such a manner that it activates the fluid connection between the pressure vessel and the measuring cell in the event of a determined exceedance of a predeterminable pressure threshold value, which exceedance is determined by means of the pressure measuring unit.

13. The device as set forth in claim 6, wherein the storage vessel is configured to be free from overpressure.

14. The device as set forth in claim 6, wherein the detection apparatus is configured for detecting the information being indicative for the zeta potential on the basis of an electric current measurement and/or on the basis of an electric voltage measurement at the measuring cell.

15. The device as set forth in claim 6, comprising an input electrode at an input of the measuring cell and an output electrode at an output of the measuring cell, wherein the detection apparatus for detecting the information being indicative for the zeta potential is formed between the input electrode and the output electrode.

16. The device as set forth in claim 15, wherein the detection apparatus is configured to detect information being indicative for an electrical resistance of the solid phase and the liquid phase in the measuring cell with the input electrode and the output electrode.

17. The device as set forth in claim 6, comprising a liquid-phase return mechanism for returning liquid phase from the storage vessel into the pressure vessel.

18. The device as set forth in claim 6, further comprising:
  a further pressure vessel, in which further liquid phase can be accommodated;
  a further measuring cell, which is arranged downstream of the further pressure vessel and such that it can be brought into fluid communication with the further pressure vessel and in which the solid phase can be accommodated;
  wherein the pressure loading apparatus is configured for loading the further pressure vessel with a pressure profile with a temporally continuous pressure change in such a manner that, as a result, further liquid phase can be conveyed out of the further pressure vessel through the further measuring cell;
  wherein the detection apparatus is configured for detecting information being indicative for the zeta potential at the further measuring cell during the loading of the further pressure vessel with the pressure profile.

19. The device as set forth in claim 6, wherein the detection apparatus is configured for detecting the information being indicative for the zeta potential whilst carrying out a baseline correction which changes over time.

20. The device as set forth in claim 6, wherein the detection apparatus is configured for detecting a base signal, which is independent of the solid phase and the liquid phase during the loading of the pressure vessel with the pressure profile; and/or wherein the pressure loading apparatus for loading the pressure vessel with a pressure profile is configured in such a manner that a pressure difference between an initial pressure value at the pressure vessel and an initial pressure value at the storage vessel is larger than one atmosphere.

* * * * *